(12) United States Patent
Chang et al.

(10) Patent No.: US 12,697,211 B2
(45) Date of Patent: Aug. 4, 2026

(54) DELIVERY CYLINDER FOR PROSTHETIC IMPLANT

(71) Applicant: EDWARDS LIFESCIENCES CORPORATION, Irvine, CA (US)

(72) Inventors: Arvin T. Chang, Yorba Linda, CA (US); Sam Sok, Santa Ana, CA (US); Amanda Kristine Anderson White, Mountain View, CA (US); Ajay Chadha, Irvine, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 190 days.

(21) Appl. No.: 18/306,705

(22) Filed: Apr. 25, 2023

(65) Prior Publication Data

US 2023/0255761 A1     Aug. 17, 2023

Related U.S. Application Data

(63) Continuation of application No. 16/818,182, filed on Mar. 13, 2020, now Pat. No. 11,666,437, which is a
(Continued)

(51) Int. Cl.
| | |
|---|---|
| *A61F 2/24* | (2006.01) |
| *A61F 2/95* | (2013.01) |
| *A61F 2/97* | (2013.01) |

(52) U.S. Cl.
CPC ............ *A61F 2/243* (2013.01); *A61F 2/2436* (2013.01); *A61F 2/2418* (2013.01); *A61F 2002/9528* (2013.01); *A61F 2/97* (2013.01)

(58) Field of Classification Search
None
See application file for complete search history.

(56) References Cited

U.S. PATENT DOCUMENTS

| | | | |
|---|---|---|---|
| 519,297 A | 5/1894 | Wanek et al. |
| 4,035,849 A | 7/1977 | Angell et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

OTHER PUBLICATIONS

Mazilu, Dumitru, Self-Expanding Stent and Delivery System for Aortic Valve Replacement, J Med Device. Dec. 2012;6 (4):410061-410069. Epub Nov. 1, 2012.

*Primary Examiner* — Shaun L David
(74) *Attorney, Agent, or Firm* — Klarquist Sparkman LLP

(57) ABSTRACT

A delivery cylinder includes a first tubular portion and a second tubular portion having a plurality of struts coupled to the first tubular portion and defining a volume for containing a radially compressed prosthetic implant. The struts include proximal end portions and main body portions extending from the proximal end portions in both an expanded configuration and a contracted configuration. The proximal end portions of each strut include a pair of first recessed portions defined in longitudinal edges of the strut, and a pair of second recessed portions defined in the longitudinal edges distally of the pair of first recessed portions. The pair of first recessed portions reduces a width of the strut to induce bending of the strut at the pair of first recessed portions, and the pair of second recessed portions reduces the width of the strut to induce bending at the pair of second recessed portions.

20 Claims, 11 Drawing Sheets

Related U.S. Application Data continuation of application No. 15/451,149, filed on Mar. 6, 2017, now Pat. No. 10,779,941.

(60) Provisional application No. 62/305,351, filed on Mar. 8, 2016.

(56)                References Cited

U.S. PATENT DOCUMENTS

| | | | |
|---|---|---|---|
| 4,592,340 A | 6/1986 | Boyles | |
| 4,955,895 A | 9/1990 | Sugiyama et al. | |
| 4,994,077 A | 2/1991 | Dobben | |
| 5,059,177 A | 10/1991 | Towne et al. | |
| 5,176,698 A | 1/1993 | Burns et al. | |
| 5,192,297 A | 3/1993 | Hull | |
| 5,266,073 A | 11/1993 | Wall | |
| 5,325,845 A | 7/1994 | Adair | |
| 5,358,496 A | 10/1994 | Ortiz et al. | |
| 5,411,552 A | 5/1995 | Andersen et al. | |
| 5,554,185 A | 9/1996 | Block et al. | |
| 5,591,195 A | 1/1997 | Taheri et al. | |
| 5,599,305 A | 2/1997 | Hermann et al. | |
| 5,632,760 A | 5/1997 | Sheiban et al. | |
| 5,639,274 A | 6/1997 | Fischell et al. | |
| 5,683,451 A | 11/1997 | Lenker et al. | |
| 5,728,068 A | 3/1998 | Leone et al. | |
| 5,749,890 A | 5/1998 | Shaknovich | |
| 5,782,809 A | 7/1998 | Umeno et al. | |
| 5,824,044 A | 10/1998 | Quiachon et al. | |
| 5,840,081 A | 11/1998 | Andersen et al. | |
| 5,908,405 A | 6/1999 | Imran et al. | |
| 5,916,147 A | 6/1999 | Boury | |
| 5,944,690 A | 8/1999 | Falwell et al. | |
| 5,961,536 A | 10/1999 | Mickley et al. | |
| 5,968,068 A | 10/1999 | Dehdashtian et al. | |
| 6,019,777 A | 2/2000 | Mackenzie | |
| 6,027,510 A | 2/2000 | Alt | |
| 6,033,381 A | 3/2000 | Kontos | |
| 6,143,016 A | 11/2000 | Bleam et al. | |
| 6,162,208 A | 12/2000 | Hipps | |
| 6,168,614 B1 | 1/2001 | Andersen et al. | |
| 6,174,327 B1 | 1/2001 | Mertens et al. | |
| 6,217,585 B1 | 4/2001 | Houser et al. | |
| 6,235,050 B1 | 5/2001 | Quiachon et al. | |
| 6,251,092 B1 | 6/2001 | Qin et al. | |
| 6,379,372 B1 | 4/2002 | Dehdashtian et al. | |
| 6,383,171 B1 | 5/2002 | Gifford et al. | |
| 6,454,799 B1 | 9/2002 | Schreck | |
| 6,458,153 B1 | 10/2002 | Bailey et al. | |
| 6,461,382 B1 | 10/2002 | Cao | |
| 6,471,672 B1 | 10/2002 | Brown et al. | |
| 6,500,147 B2 | 12/2002 | Omaleki et al. | |
| 6,514,228 B1 | 2/2003 | Hamilton et al. | |
| 6,527,979 B2 | 3/2003 | Constantz et al. | |
| 6,579,305 B1 | 6/2003 | Lashinski | |
| 6,582,462 B1 | 6/2003 | Andersen et al. | |
| 6,652,578 B2 | 11/2003 | Bailey et al. | |
| 6,730,118 B2 | 5/2004 | Spenser et al. | |
| 6,733,525 B2 | 5/2004 | Yang et al. | |
| 6,764,504 B2 | 7/2004 | Wang et al. | |
| 6,767,362 B2 | 7/2004 | Schreck | |
| 6,827,731 B2 | 12/2004 | Armstrong et al. | |
| 6,830,584 B1 | 12/2004 | Seguin | |
| 6,893,460 B2 | 5/2005 | Spenser et al. | |
| 6,908,481 B2 | 6/2005 | Cribier | |
| 7,011,094 B2 | 3/2006 | Rapacki et al. | |
| 7,018,406 B2 | 3/2006 | Seguin et al. | |
| 7,018,408 B2 | 3/2006 | Bailey et al. | |
| 7,137,993 B2 | 11/2006 | Acosta et al. | |
| 7,276,084 B2 | 10/2007 | Yang et al. | |
| 7,318,278 B2 | 1/2008 | Zhang et al. | |
| 7,320,702 B2 | 1/2008 | Hammersmark et al. | |
| 7,320,704 B2 | 1/2008 | Lashinski et al. | |
| 7,374,571 B2 | 5/2008 | Pease et al. | |
| 7,393,360 B2 | 7/2008 | Spenser et al. | |
| 7,435,257 B2 | 10/2008 | Lashinski et al. | |
| 7,510,575 B2 | 3/2009 | Spenser et al. | |
| 7,585,321 B2 | 9/2009 | Cribier | |
| 7,594,926 B2 | 9/2009 | Linder et al. | |
| 7,597,709 B2 | 10/2009 | Goodin | |
| 7,618,446 B2 | 11/2009 | Andersen et al. | |
| 7,749,266 B2 | 7/2010 | Forster et al. | |
| 7,780,723 B2 | 8/2010 | Taylor | |
| 7,785,366 B2 | 8/2010 | Maurer et al. | |
| 7,959,661 B2 | 6/2011 | Hijlkema et al. | |
| 7,993,394 B2 | 8/2011 | Hariton et al. | |
| 8,029,556 B2 | 10/2011 | Rowe | |
| 8,167,932 B2 | 5/2012 | Bourang et al. | |
| RE43,882 E | 12/2012 | Hopkins et al. | |
| 8,449,606 B2 | 5/2013 | Eliasen et al. | |
| 8,460,368 B2 | 6/2013 | Taylor et al. | |
| 8,475,523 B2 | 7/2013 | Duffy | |
| 8,512,401 B2 | 8/2013 | Murray, III et al. | |
| 8,562,673 B2 | 10/2013 | Yeung et al. | |
| 8,568,472 B2 | 10/2013 | Marchand et al. | |
| 8,652,145 B2 | 2/2014 | Maimon et al. | |
| 8,652,202 B2 | 2/2014 | Alon et al. | |
| 8,702,782 B2 | 4/2014 | Zilla et al. | |
| 8,728,153 B2 | 5/2014 | Bishop et al. | |
| 8,790,387 B2 | 7/2014 | Nguyen et al. | |
| 8,852,271 B2 | 10/2014 | Murray, III et al. | |
| 8,986,361 B2 | 3/2015 | Bortlein et al. | |
| 9,061,119 B2 | 6/2015 | Le et al. | |
| 9,119,716 B2 | 9/2015 | Lee et al. | |
| 9,155,619 B2 | 10/2015 | Liu et al. | |
| 9,168,131 B2 | 10/2015 | Yohanan et al. | |
| 9,795,477 B2 | 10/2017 | Tran et al. | |
| 9,867,700 B2 | 1/2018 | Bakis et al. | |
| 11,273,038 B2 | 3/2022 | Tang et al. | |
| 2001/0002445 A1 | 5/2001 | Vesely | |
| 2001/0007082 A1 | 7/2001 | Dusbabek et al. | |
| 2002/0032481 A1 | 3/2002 | Gabbay | |
| 2002/0058995 A1 | 5/2002 | Stevens | |
| 2002/0165461 A1 | 11/2002 | Hayzelden et al. | |
| 2003/0040792 A1 | 2/2003 | Gabbay | |
| 2003/0050694 A1 | 3/2003 | Yang et al. | |
| 2003/0100939 A1* | 5/2003 | Yodfat | A61F 2/958 |
| | | | 606/108 |
| 2003/0120341 A1 | 6/2003 | Shennib et al. | |
| 2004/0093061 A1 | 5/2004 | Acosta et al. | |
| 2004/0133263 A1 | 7/2004 | Dusbabek et al. | |
| 2004/0143197 A1 | 7/2004 | Soukup et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0080474 A1 | 4/2005 | Andreas et al. | |
| 2005/0096736 A1 | 5/2005 | Osse et al. | |
| 2005/0113910 A1 | 5/2005 | Paniagua et al. | |
| 2005/0137686 A1 | 6/2005 | Salahieh et al. | |
| 2005/0137689 A1 | 6/2005 | Salahieh et al. | |
| 2005/0137693 A1 | 6/2005 | Haug et al. | |
| 2005/0137697 A1 | 6/2005 | Salahieh et al. | |
| 2005/0149160 A1 | 7/2005 | McFerran | |
| 2005/0203614 A1 | 9/2005 | Forster et al. | |
| 2005/0203617 A1 | 9/2005 | Forster et al. | |
| 2005/0245894 A1 | 11/2005 | Azizi | |
| 2006/0025857 A1 | 2/2006 | Bergheim et al. | |
| 2006/0184226 A1* | 8/2006 | Austin | A61F 2/95 |
| | | | 623/1.11 |
| 2006/0282150 A1 | 12/2006 | Olson et al. | |
| 2006/0287719 A1 | 12/2006 | Rowe et al. | |
| 2007/0005131 A1 | 1/2007 | Taylor | |
| 2007/0073389 A1 | 3/2007 | Bolduc et al. | |
| 2007/0088431 A1 | 4/2007 | Bourang et al. | |
| 2007/0100356 A1 | 5/2007 | Lucatero et al. | |
| 2007/0112422 A1 | 5/2007 | Dehdashtian | |
| 2007/0203575 A1 | 8/2007 | Forster et al. | |
| 2007/0213813 A1 | 9/2007 | Von Segesser et al. | |
| 2007/0219612 A1 | 9/2007 | Andreas et al. | |
| 2007/0239254 A1 | 10/2007 | Chia et al. | |
| 2007/0244546 A1 | 10/2007 | Francis | |
| 2007/0265700 A1 | 11/2007 | Eliasen et al. | |
| 2008/0065011 A1 | 3/2008 | Marchand et al. | |
| 2008/0082165 A1 | 4/2008 | Wilson et al. | |
| 2008/0103520 A1 | 5/2008 | Selkee | |

(56)                 References Cited

U.S. PATENT DOCUMENTS

| | | |
|---|---|---|
| 2008/0125853 A1 | 5/2008 | Bailey et al. |
| 2008/0132989 A1 | 6/2008 | Snow et al. |
| 2008/0188928 A1 | 8/2008 | Salahieh et al. |
| 2008/0294230 A1 | 11/2008 | Parker |
| 2009/0024428 A1 | 1/2009 | Hudock |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0191326 A1 | 7/2010 | Alkhatib |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0022165 A1* | 1/2011 | Oba ..................... A61F 2/2427 623/2.11 |
| 2011/0054596 A1 | 3/2011 | Taylor |
| 2011/0137331 A1 | 6/2011 | Walsh et al. |
| 2011/0160846 A1 | 6/2011 | Bishop et al. |
| 2011/0245917 A1 | 10/2011 | Savage et al. |
| 2011/0251682 A1 | 10/2011 | Murray, III et al. |
| 2012/0123529 A1 | 5/2012 | Levi et al. |
| 2012/0209375 A1 | 8/2012 | Madrid et al. |
| 2012/0239142 A1 | 9/2012 | Liu et al. |
| 2013/0030519 A1 | 1/2013 | Tran et al. |
| 2013/0138207 A1 | 5/2013 | Quadri et al. |
| 2013/0310923 A1 | 11/2013 | Kheradvar et al. |
| 2013/0317598 A1 | 11/2013 | Rowe et al. |
| 2013/0345796 A1 | 12/2013 | Eidenschink |
| 2014/0046435 A1 | 2/2014 | Yeung et al. |
| 2014/0163670 A1 | 6/2014 | Alon et al. |
| 2014/0296962 A1 | 10/2014 | Cartledge et al. |
| 2015/0157455 A1 | 6/2015 | Hoang et al. |
| 2015/0238315 A1 | 8/2015 | Rabito et al. |
| 2016/0015543 A1 | 1/2016 | Perouse et al. |
| 2016/0113768 A1 | 4/2016 | Ganesan et al. |
| 2017/0056149 A1 | 3/2017 | Rajpara et al. |
| 2017/0065415 A1 | 3/2017 | Rupp et al. |
| 2017/0128197 A1 | 5/2017 | Bialas et al. |
| 2017/0156839 A1 | 6/2017 | Cooper et al. |
| 2017/0156859 A1 | 6/2017 | Chang et al. |
| 2017/0231765 A1 | 8/2017 | Desrosiers et al. |
| 2018/0153689 A1 | 6/2018 | Maimon et al. |
| 2018/0344456 A1 | 12/2018 | Barash et al. |

FOREIGN PATENT DOCUMENTS

| | | |
|---|---|---|
| EP | 0592410 B1 | 10/1995 |
| EP | 0850607 A1 | 7/1998 |
| EP | 1796597 A2 | 6/2007 |
| FR | 2815844 A1 | 5/2002 |
| WO | 9117720 A1 | 11/1991 |
| WO | 1991017720 A1 | 11/1991 |
| WO | 9829057 A1 | 7/1998 |
| WO | 1998029057 A1 | 7/1998 |
| WO | 1999012483 A1 | 3/1999 |
| WO | 0149213 A2 | 7/2001 |
| WO | 2001049213 A2 | 7/2001 |
| WO | 0154625 A1 | 8/2001 |
| WO | 2001054625 A1 | 8/2001 |
| WO | 0176510 A2 | 10/2001 |
| WO | 2001076510 A2 | 10/2001 |
| WO | 0222054 A1 | 3/2002 |
| WO | 2002022054 A1 | 3/2002 |
| WO | 0236048 A1 | 5/2002 |
| WO | 2002036048 A1 | 5/2002 |
| WO | 0247575 A2 | 6/2002 |
| WO | 2002047575 A2 | 6/2002 |
| WO | 2002060352 A1 | 8/2002 |
| WO | 2003030776 A2 | 4/2003 |
| WO | 03047468 A1 | 6/2003 |
| WO | 2003047468 A1 | 6/2003 |
| WO | 2004019825 A1 | 3/2004 |
| WO | 2005084595 A1 | 9/2005 |
| WO | 2005102015 A2 | 11/2005 |
| WO | 2006032051 A2 | 3/2006 |
| WO | 2006111391 A1 | 10/2006 |
| WO | 2006138173 A2 | 12/2006 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |
| WO | 2015063118 A1 | 5/2015 |

* cited by examiner

DELIVERY CYLINDER FOR PROSTHETIC IMPLANT

CROSS REFERENCE TO RELATED APPLICATIONS

This application is a continuation of U.S. application Ser. No. 16/818,182, filed Mar. 13, 2020, which is a continuation of U.S. application Ser. No. 15/451,149, filed Mar. 6, 2017, which claims the benefit of U.S. Provisional Application No. 62/305,351, filed Mar. 8, 2016. Each of the above-listed applications is incorporated herein by reference in its entirety.

FIELD

This application relates to delivery assemblies for prosthetic implants such as transcatheter heart valves.

BACKGROUND

Prosthetic implants such as self-expanding transcatheter heart valves are typically housed in a delivery cylinder that constrains the prosthetic valve to maintain it in a radially compressed state. Such delivery cylinders typically have a relatively small diameter to facilitate insertion of the delivery cylinder through an introducer sheath into the body and through narrow vessels toward an implantation site. While the valve is contained in the delivery cylinder, the valve exerts radial force against the walls of the delivery cylinder. During deployment of the prosthetic valve, the valve can be partially advanced from the delivery cylinder and retracted into the delivery cylinder or recaptured as needed to properly position the valve in the native annulus. The recapture process can exert substantial axial or columnar force on the delivery cylinder as the prosthetic valve is urged back into the radially compressed state by the walls of the delivery cylinder. Making the walls of the delivery cylinder strong enough to withstand the radial forces exerted by the valve in the compressed state and the axial forces exerted during valve recapture results in an increased diameter of the delivery assembly, which can complicate insertion and access to the implantation site. Accordingly, improvements to delivery cylinders for prosthetic implants are desirable.

SUMMARY

This summary is meant to provide some examples and is not intended to be limiting of the scope of the disclosure in any way. For example, any feature included in an example of this summary is not required by the claims, unless the claims explicitly recite the features. Also, the features, steps, concepts, etc. described in examples in this summary and elsewhere in this disclosure can be combined in a variety of ways.

Certain embodiments of the disclosure concern delivery cylinders for prosthetic implants and methods of using the same. A delivery cylinder for a prosthetic implant can comprise a first tubular portion and a second tubular portion. The second tubular portion can comprise a plurality of strut members coupled to the first tubular portion and defining a volume for containing the prosthetic implant in a radially compressed state. The strut members can include respective flex regions configured such that application of force to the strut members causes deformation of the flex regions and corresponding radially inward or outward movement of the strut members relative to a longitudinal axis of the delivery cylinder between an expanded configuration and a contracted configuration. The delivery cylinders can include any of the features or components described here or described elsewhere in this application.

An assembly and/or system can comprise a shaft having a proximal end portion and a distal end portion, and a delivery cylinder (e.g., the delivery cylinder described above or any of the delivery cylinders described elsewhere in this application) coupled to the distal end portion of the shaft and including a plurality of strut members defining a tubular portion. The strut members can include respective flex regions configured such that application of force to the strut members causes deformation of the flex regions and corresponding radially inward or outward movement of the strut members relative to a longitudinal axis of the delivery apparatus between an expanded configuration and a contracted configuration. The assembly and/or system can further comprise a prosthetic implant retained in a radially compressed state in the delivery cylinder. The assembly and/or system can include any of the features or components described here or described elsewhere in this application.

Various methods can comprise deploying a prosthetic implant in a radially compressed state from a delivery cylinder (e.g., the delivery cylinder described above or any of the delivery cylinders described elsewhere in this application) including a plurality of circumferentially arranged strut members such that the prosthetic implant at least partially expands to a functional size and the strut members move radially inwardly from an expanded configuration to a contracted configuration. The method(s) can further comprise recapturing the prosthetic implant such that the prosthetic implant is at least partially returned to the radially compressed state by the delivery cylinder, and the strut members move radially outwardly such that the delivery cylinder returns to the expanded configuration. The method(s) can also include any of the steps described here or described elsewhere in this application.

Various methods can comprise inserting a delivery assembly including a delivery cylinder (e.g., the delivery assemblies/systems and delivery cylinders described above or any of the delivery assemblies/systems and delivery cylinders described elsewhere in this application) containing a prosthetic implant in a radially compressed state into an introducer sheath such that a plurality of circumferentially arranged strut members of the delivery cylinder move radially inwardly from an expanded configuration to a contracted configuration to conform to a diameter of the introducer sheath. The method(s) can further comprise advancing the delivery apparatus through the introducer sheath and into a patient's body such that the strut members move radially outwardly and return to the expanded configuration. The method(s) can also include any of the steps described here or described elsewhere in this application.

The foregoing and other objects, features, and advantages of the disclosed technology will become more apparent from the following detailed description, which proceeds with reference to the accompanying figures.

BRIEF DESCRIPTION OF THE DRAWINGS

Various embodiments are depicted in the accompanying drawings for illustrative purposes, and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below.

Figures 1, 2:
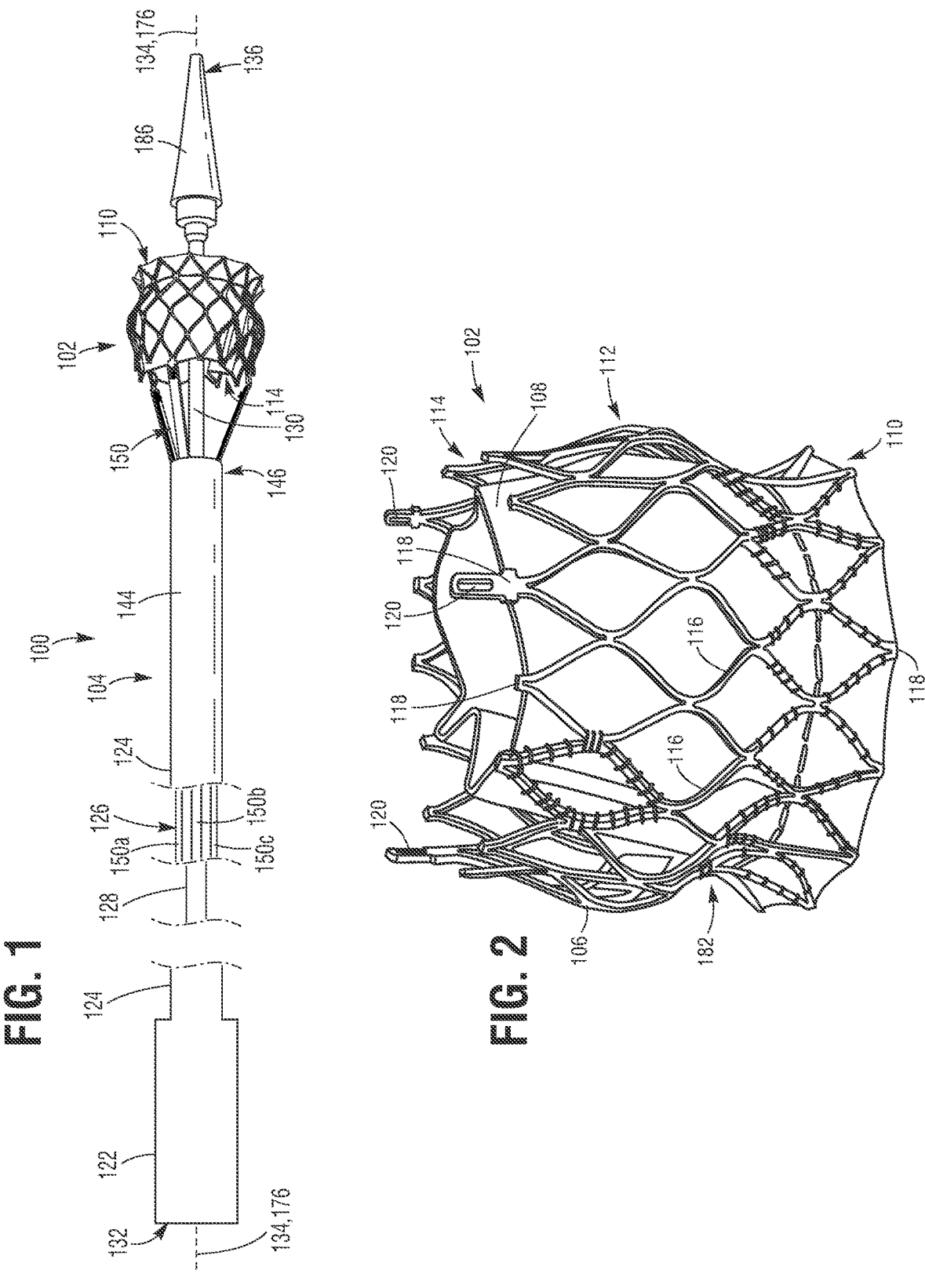
FIG. 1 is a perspective view of a representative embodiment of a prosthetic implant delivery device.
FIG. 2 is a perspective view of the prosthetic implant of the delivery assembly of FIG. 1.

FIG. 1 illustrates an exemplary embodiment of a prosthetic implant delivery assembly 100 that can be adapted to deliver and implant a prosthetic implant, such as a transcatheter heart valve, in a tubular organ or passageway in the body, such as a native valve annulus of the heart. In the illustrated embodiment, the delivery assembly 100 can comprise a prosthetic heart valve 102 releasably coupled to a delivery apparatus 104.

A wide variety of prosthetic implants/valves can be used with the delivery assemblies, apparatuses, cylinders, systems, etc. described herein, including self-expandable implants/valves, balloon-expandable implants/valves, mechanically-expandable implants/valves, stents, grafts, etc. and/or a combinations of some or all of these. Referring now to FIG. 2, the prosthetic valve 102 is a non-limiting example of an implant/valve that can be used. The prosthetic valve 102 can comprise an annular stent or frame 106 and a valve structure 108 which is coupled to the frame 106. The prosthetic valve 102 can have in inflow end portion 110, an intermediate portion 112, and an outflow end portion 114.

The frame 106 can comprise a plurality of interconnected struts 116 arranged in a lattice-type pattern and forming a plurality of apices 118 at the inflow and outflow ends 110, 114 of the prosthetic valve 102. All or at least some of the apices 118 at the outflow end 114 of the prosthetic valve 102 can have a respective aperture or opening 120 formed therein (e.g., three in the illustrated embodiment). In one embodiment, none of the apices 118 include an aperture or opening 120. In implants where openings 120 are included, the openings 120 can be used to, for example, releasably couple the prosthetic valve 102 to the delivery apparatus 104. In implants where no openings 120 are included, other ways of releasably coupling the prosthetic valve 102 to the delivery apparatus 104, e.g., one or more sutures releasably passing through cells of the frame can be used and/or other coupling elements can be used.

The apices 118 having the openings 120 can be arranged in various ways relative to each other and relative to the other apices 118 at the outflow end 114 of the prosthetic valve 102. For example, the apices 118 having the openings 120 can be uniformly (e.g., symmetrically) distributed circumferentially around the outflow end 114 of the prosthetic valve 102 relative to the other apices 118 at the outflow end 114 of the prosthetic valve 102. The apices 118 with the openings 120 can be referred to as connecting arms, or connecting posts, extensions, and can be longer than the apices without the openings 120.

The frame 106 can be made of any of various suitable plastically-expandable materials (e.g., stainless steel, etc.) or self-expanding materials (e.g., shape memory materials, nickel titanium alloy ("NiTi"), such as Nitinol). When constructed of a plastically-expandable material, the frame 106 (and thus the prosthetic valve 102) can be crimped to a radially collapsed configuration or state on a delivery catheter and then expanded to a functional size inside a patient by an inflatable balloon or equivalent expansion mechanism. When constructed of a self-expandable material, the frame 106 (and thus the prosthetic valve 102) can be crimped to a radially collapsed configuration and restrained in the collapsed configuration by insertion into a sheath or equivalent mechanism of a delivery catheter. Once inside the body, the prosthetic valve can be deployed from the delivery sheath, and the prosthetic valve can radially expand to its functional size.

Further details regarding collapsible transcatheter prosthetic heart valves, including the manner in which the valve structure 108 can be coupled to the frame 106 of the prosthetic valve 102 can be found, for example, in U.S. Pat. Nos. 6,730,118, 7,393,360, 7,510,575, 7,993,394, and 8,652, 202, which are incorporated herein by reference in their entirety.

Referring again to FIG. 1, the delivery apparatus 104 can comprise a handle 122, an outer catheter 124, a release catheter 126, and a locking catheter 128. The handle 122 can be disposed at the proximal end portion 132 of the delivery apparatus 104. The outer catheter 124, the release catheter 126, and the locking catheter 128 can extend coaxially along a longitudinal axis 134 from the proximal end 132 of the delivery apparatus 104 toward an opposite, distal end portion 136 of the delivery apparatus 104. The release catheter 126 and the locking catheter 128 can be disposed coaxially within and extend through a lumen of the outer catheter 124. The locking catheter 128 can be disposed coaxially within and extend through a lumen of the release catheter 126.

The outer catheter 124 can comprise a sheath portion 144 disposed at a distal end 146 of the outer catheter 124. The sheath 144 can be used to retain the prosthetic valve 102 in a radially compressed state during delivery of the prosthetic valve 102 through a patient's body, as further described below. In the illustrated embodiment, the outer catheter 124, the release catheter 126, and the locking catheter 128 can each be independently moveable relative to each other by, for example, actuation of one or more controls on the handle 122.

The release catheter 126 can include a plurality of tines or arms 150*a*, 150*b*, 150*c*, collectively referred to as arms 150. The arms 150 can releasably engage the prosthetic valve 102 at, for example, the openings 120 of select apices 118 of the prosthetic valve (see, e.g., FIG. 2). In some embodiments, the arms 150 can be independently movable in the axial direction to position the prosthetic valve 102 (e.g., to orient a longitudinal axis 176 of the prosthetic valve at an angle to the longitudinal axis 134 of the delivery apparatus). An inner catheter 130 can be disposed coaxially within the release catheter 126, and can comprise a nose cone 186 located at the distal end of the inner catheter.

Figure 3:
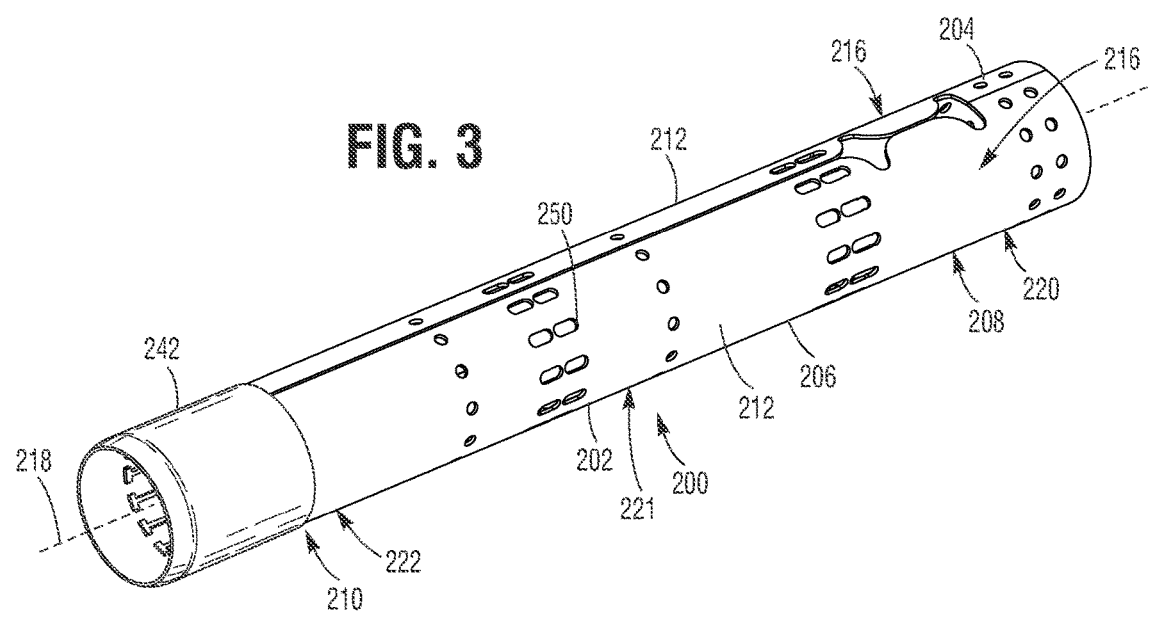
FIGS. 3 and 4 are perspective views of a representative embodiment of a delivery cylinder including two strut members.

FIG. 3 illustrates a representative embodiment of a delivery cylinder 200 that can be used in combination with any of the delivery assemblies/systems, and/or implants described herein. The delivery cylinder can include a main body portion 202 having a first proximal tubular portion 204 and a second distal tubular portion 206. In some embodiments, the first tubular portion 204 can be coupled to a distal end portion of an outer catheter, such as outer catheter 124 of FIG. 1. The second tubular portion 206 can include a proximal end portion 208 and a distal end portion 210, and a plurality of circumferentially arranged strut members 212. The strut members 212 can also comprise respective main body portions 221 and proximal and distal end portions 220, 222. In the illustrated embodiment, the proximal end portions 220 can be coupled to the first tubular portion 204. In some embodiments, the strut members 212 can be integrally formed with the first tubular portion 204 such that the first tubular portion and the respective strut members are a one-piece unitary construction. Alternatively, the strut members 212 can be separately formed and coupled to the first tubular portion 204 by, for example, welding.

As shown, for example, in the illustrated embodiment, the strut members 212 can define a chamber or volume 214 (see, e.g., FIGS. 4, 5, and 6) for containing a prosthetic implant, such as the valve 102 of FIG. 2, in a radially compressed delivery state. In the embodiment illustrated in FIGS. 3 and 4, the second tubular portion 206 includes two concave-convex strut members 212. However, it should be understood that the second tubular portion can include any suitable number of strut members having any suitable shape. For example, the delivery cylinder can have 2-20 strut members, e.g., four strut members (see, e.g., FIGS. 8-10), twelve strut members (FIG. 19), etc., which can be curved or planar or another shape, according to the particular application. The strut members 212 can also include a plurality of openings 250 at different locations along the length of the strut members and circumferentially spaced around the strut members to secure, for example, a woven liner to the strut members, as further described below.

In the illustrated embodiment, the delivery cylinder can also include a flexible member or sleeve 242 coupled to the distal end portions of the strut members and configured to, for example, elastically deform upon insertion of a prosthetic implant into the delivery cylinder to reduce damage to the implant. The flexible member 242 can be made from any suitable pliable biocompatible material, such as polyurethane or silicone.

Figure 4:
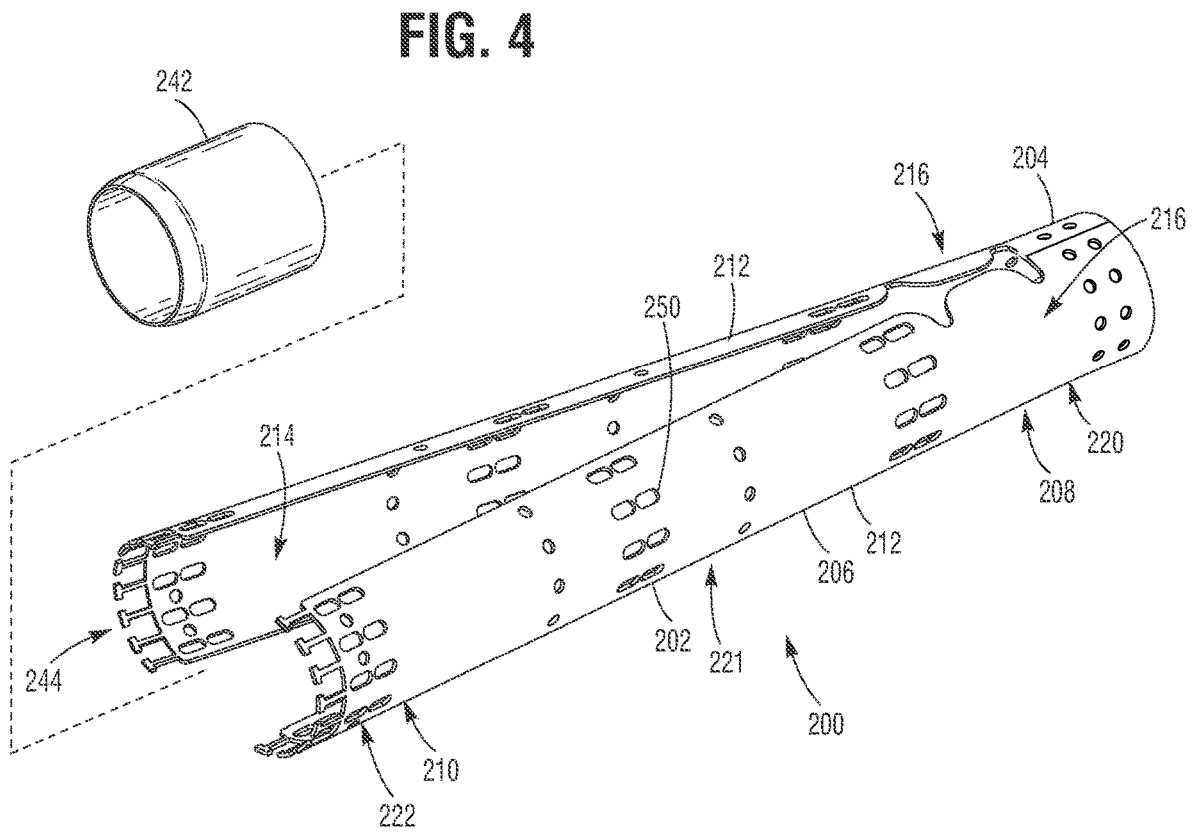
Figures 5, 6:
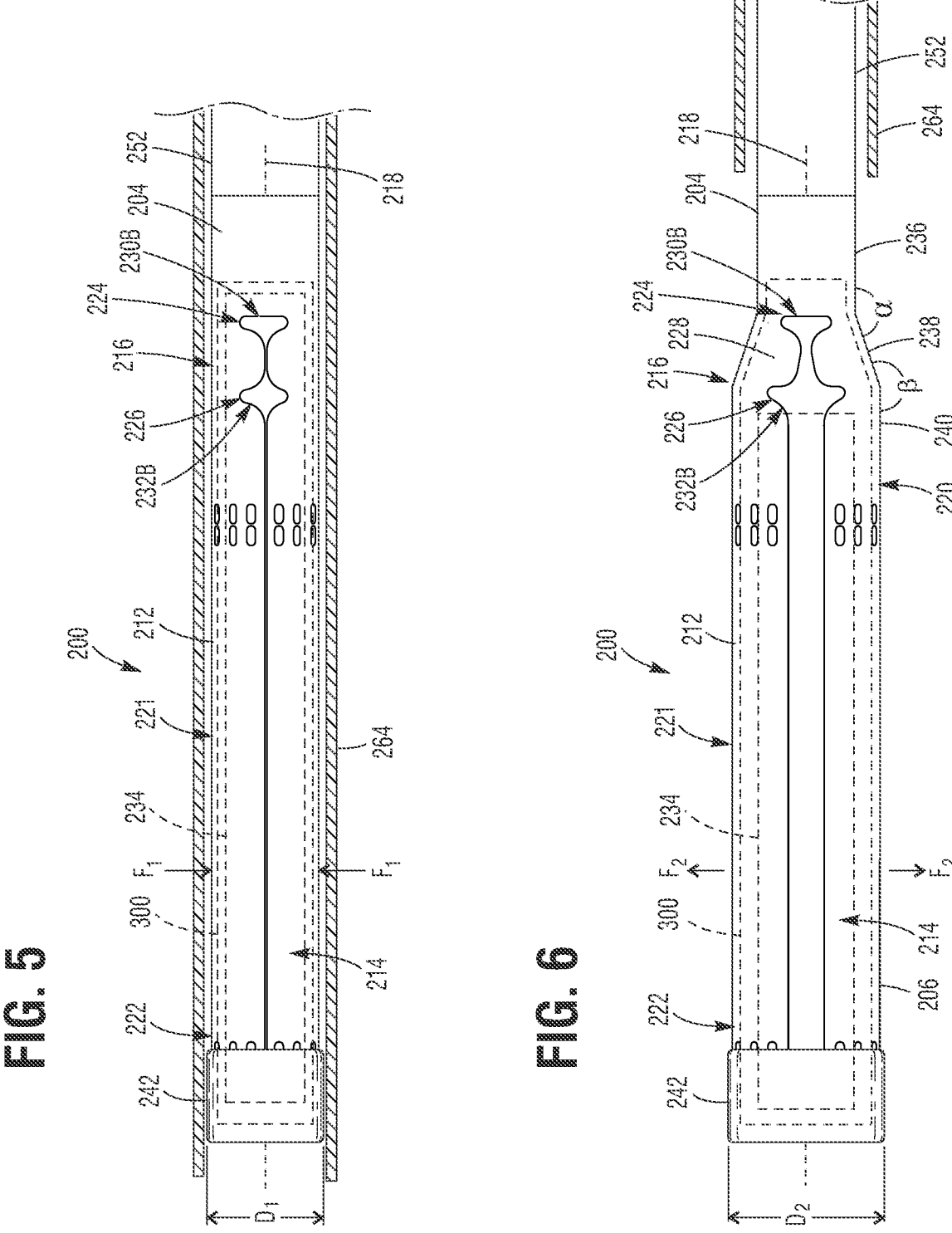
FIG. 5 is a side-elevation view of the delivery cylinder of FIG. 3 in a contracted position within an introducer sheath.
FIG. 6 is a side-elevation view of the delivery cylinder of FIG. 3 in an expanded configuration.

Referring to FIGS. 3-9, the strut members 212 can include respective flex regions 216. In the illustrated embodiment, the flex regions 216 are located at the proximal end portions 220 of the strut members, and can be configured to flex, bend, or otherwise deform such that the strut members are movable between a collapsed or contracted configuration (FIG. 5) and an expanded configuration (FIG. 6). In the illustrated embodiment, the flex regions 216 of the strut members can include respective first and second bending portions 224, 226 separated by intermediate portions 228.

Figure 7:
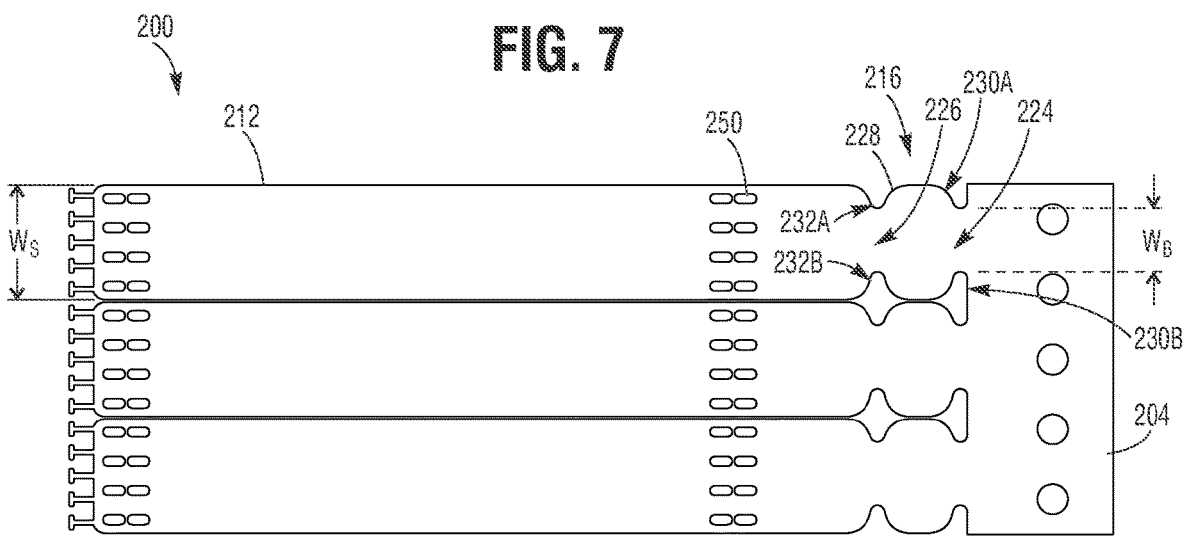
FIG. 7 is a plan view of another embodiment of a delivery cylinder including three strut members flattened for purposes of illustration.
Figure 8:
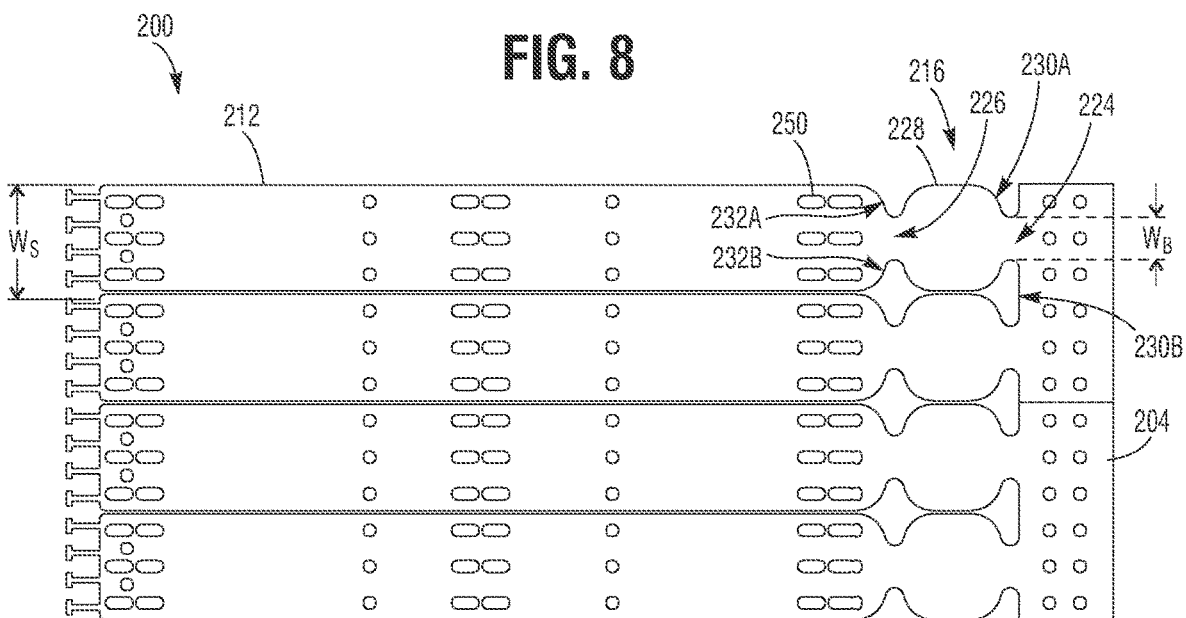
FIG. 8 is a plan view of another embodiment of a delivery cylinder including four strut members flattened for purposes of illustration.

FIGS. 7 and 8 illustrate the bending portions 224, 226 in greater detail in the context of three- and four-strut member delivery cylinder embodiments, respectively, shown unrolled or flattened for purposes of illustration. As shown in FIGS. 7 and 8, the first bending portions 224 can be located adjacent the first tubular portion 204, and can be defined by first cut-out or recessed portions 230A, 230B located on the sides of the strut members 212. The recessed portions 230A, 230B can reduce a width of the respective strut members at the location of the first bending portion 224 such that the strut members 212 can be induced to bend at the first bending portion when radial force is applied to the strut members (see, e.g., FIGS. 5 and 6).

For example, in some embodiments, a width $W_B$ of the first bending portions 224 can be from about 20% to about 90% of a width $W_S$ of the strut members 212. In the three-strut configuration illustrated in FIG. 7, the width $W_B$ of the first bending portions is about 60% of the width $W_S$ of the strut members. In the four-strut configuration of FIG. 8, the width $W_B$ of the first bending portions is about 40% of the width $W_S$ of the strut members, although it should be appreciated that the bending portions can have any suitable width depending upon the number of strut members, the flexural strength required, etc.

The second bending portions 226 can be defined by second cut-out or recessed portions 232A, 232B defined in the sides of the strut members distally of the first recessed portions. The second recessed portions 232A, 232B can be configured to induce the strut members to bend at the second bending portions 226 when radial force is applied to the strut members. In the illustrated embodiments, the respective widths of the first and second bending portions 224, 226 are substantially equal to one another. However, it should be appreciated that in alternative embodiments, the widths of the first and second bending portions can be different from one another. Additionally, the widths of the bending portions can also be different between respective strut members, as desired. Furthermore, although the first bending portions 224 and the second bending portions 226 of the respective strut members are located at substantially the same location along the lengths of the strut members as the respective first and second bending portions of the other strut members, it should be understood that the first and second bending portions can be located at different locations along the lengths of the strut members from one strut member to another. Further, in alternative embodiments, the bending portions 224, 226 need not comprise the respective recessed portions 230A-230B, 232A-232B (see, e.g., FIG. 12).

Referring again to FIGS. 5 and 6, bending of the strut members 212 at the first and second bending portions 224, 226 can allow the second tubular portion 206 to radially expand and contract depending upon the radial forces exerted upon the strut members. For example, FIG. 5 illustrates the delivery cylinder 200 within a lumen of an introducer sheath 264 (shown in cross-section and spaced apart from the delivery cylinder for purposes of illustration) and coupled to an outer catheter 252. The introducer sheath 264 can constrain the delivery cylinder and exert radially inward forces $F_1$ on the strut members 212 such that the flex regions 216 flex or deform, causing the strut members 212 to move radially inward or toward the longitudinal axis 218 of the delivery cylinder into the contracted configuration. Thus, in the contracted configuration, the second tubular portion 206 can have a first diameter $D_1$, which can be substantially equal to an inner diameter of the introducer sheath 264. Movement of the strut members to the contracted configuration can also cause corresponding radial compression of a prosthetic implant schematically illustrated at 234 contained in the second tubular portion 206 as the diameter of the second tubular portion is reduced.

Referring to FIG. 6, as the delivery cylinder is advanced from the introducer sheath 264, radially outward force(s) indicated at $F_2$ applied to the strut members 212 (e.g., by the compressed prosthesis 234) and/or the shape-memory of the strut members can cause the flex regions 216 to flex or deform such that the strut members move radially outward or away from the longitudinal axis 218 of the delivery cylinder into the expanded configuration. This radially outward movement of the strut members 212 can cause the diameter of the second tubular portion 206 to increase from the first diameter $D_1$ to a second diameter $D_2$ in proportion to the distance moved by the strut members. More particularly, application of radially outward force $F_2$ can cause the first bending portions 224 of the strut members to bend radially away from the longitudinal axis 218 such that an angle α (FIG. 6) defined between an exterior surface 236 of the first tubular portion 204 (or the outer catheter where the delivery cylinder is integrally formed with the outer catheter) and an exterior surface 238 of the respective intermediate portions 228 is less than 180 degrees.

Meanwhile the second bending portions 226 can bend in a direction radially toward the longitudinal axis such that an angle β defined between the respective exterior surfaces 238 of the intermediate portions 228 and respective exterior surfaces 240 of the main portions 221 of the strut members is greater than 180 degrees. In this manner, the intermediate portions 228 can be angled relative to the longitudinal axis 218 of the delivery cylinder when the strut members are in the expanded configuration, while the main portions 221 of the strut members can be substantially parallel to the longitudinal axis. In the illustrated configuration, a diameter of the flexible member 242 can also change between the first diameter $D_1$ and the second diameter $D_2$ as the second tubular portion 206 moves from the contracted configuration to the expanded configuration. In some embodiments, the flexible member can also limit radial expansion of the strut members. When the radially outward forces $F_2$ are relieved (e.g., by deploying the prosthesis 234), the flex regions 216 can flex or deform such that the strut members 212 return to the collapsed configuration illustrated in FIG. 5.

In some embodiments, $D_1$ can be about 3 mm to about 6 mm, being a specific example. In some embodiments, $D_1$ can be about 4 mm to about 5 mm. In certain embodiments, $D_2$ can be about 1% greater than $D_1$, about 3% greater than $D_1$, about 5% greater than $D_1$, about 10% greater than $D_1$, about 20% greater than $D_1$, about 50% greater than $D_1$, or about 100% greater than $D_1$.

Figure 9:
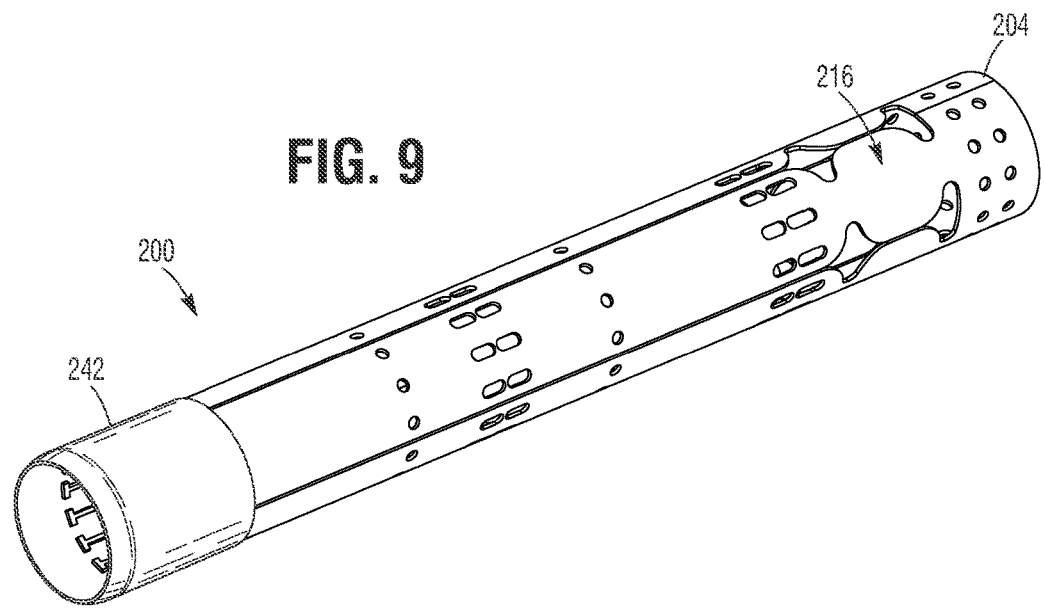
FIGS. 9 and 10 are perspective views of the delivery cylinder of FIG. 8.
Figure 10:
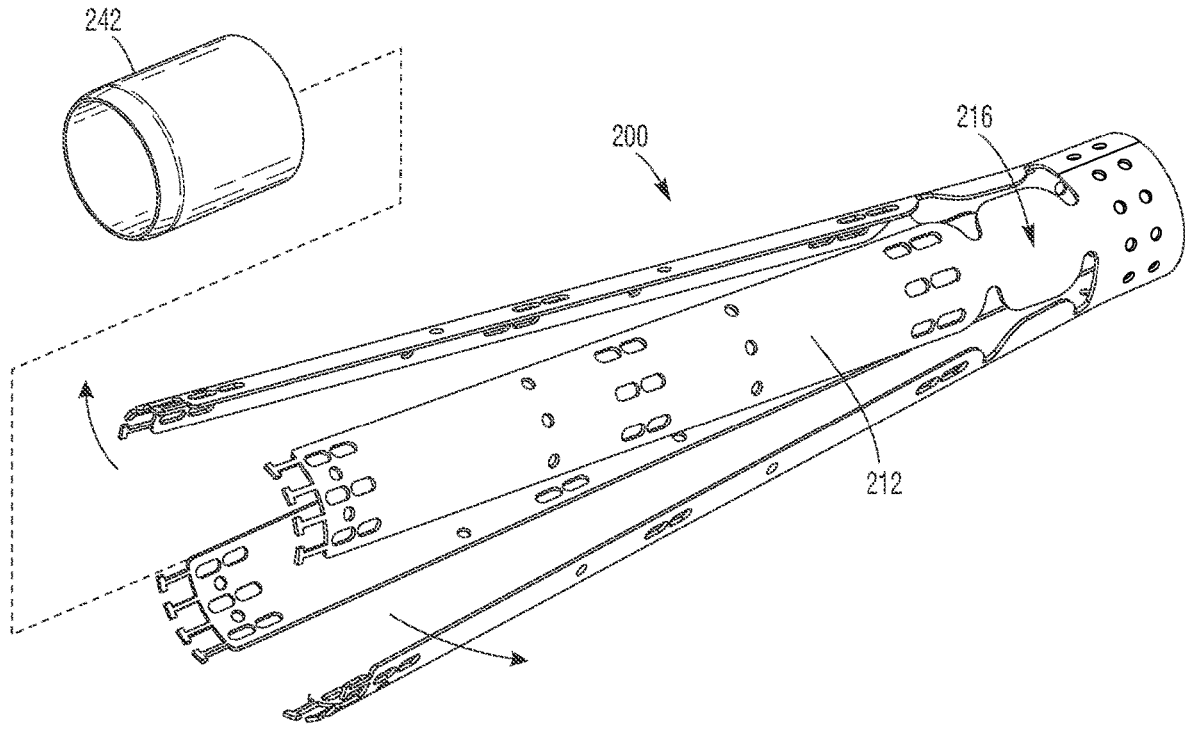
Figure 11:
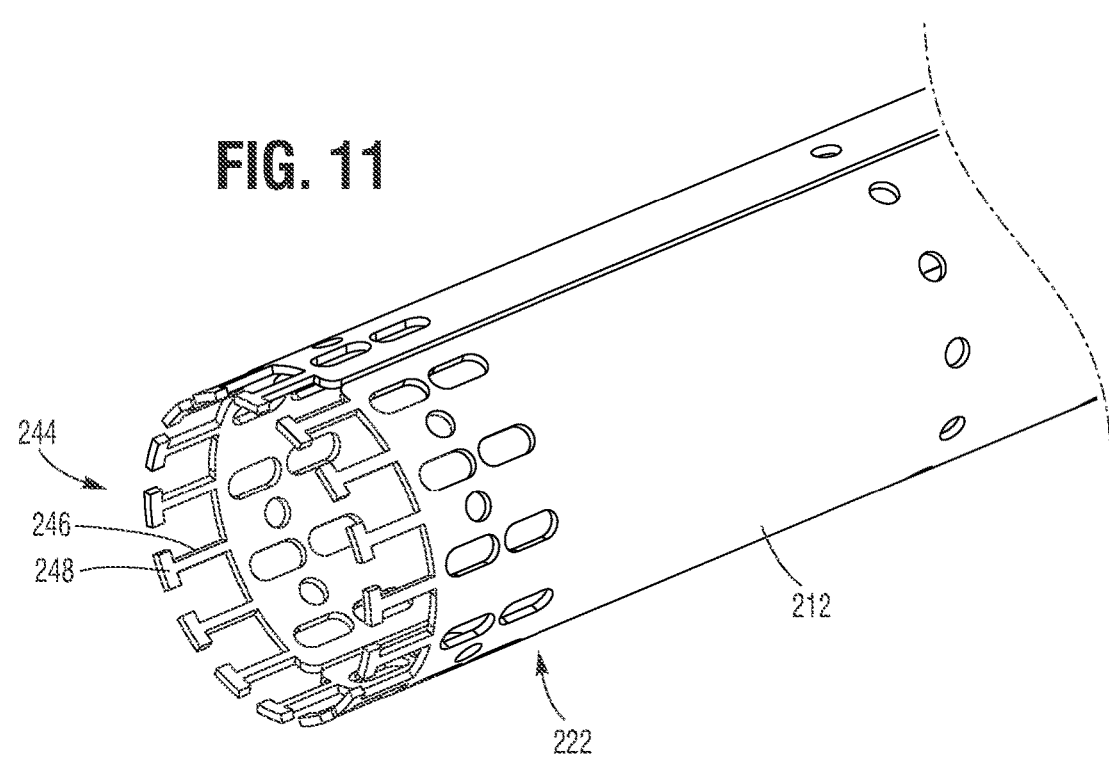
FIG. 11 is a perspective view of a distal end portion of the delivery cylinder of FIG. 3.

Referring to FIGS. 9, 10, and 11, the flexible member 242 can be retained on the distal end portions 222 of the of the strut members 212 by retaining mechanisms 244 (FIGS. 4, 11). In the illustrated embodiment, the retaining mechanisms 244 are a plurality of extension portions 246 extending longitudinally from the distal end portions of the strut members 212 and including tip portions 248 having a longitudinal axis perpendicular to the extension portions 246. The extension portions 246 can be positioned against an interior surface of the flexible member 242, or can be embedded within the flexible member. In this manner, the tip portions 248 can resist longitudinal movement of the flexible member to reduce or prevent, for example, detachment of the flexible member during deployment of the prosthetic device. In some embodiments, the extension portions 246 can be configured to bend or deflect radially outwardly with the flexible member to, for example, facilitate recapture of the prosthetic device into the delivery cylinder as described in detail below. In some embodiments, the retaining mechanisms 244 need not comprise the tip portions 248. Furthermore, it should be understood that the distal end portions of the strut members can include any suitable number of extension portions having any suitable width dimension depending upon the strength and/or flexibility properties desired.

Figure 12:
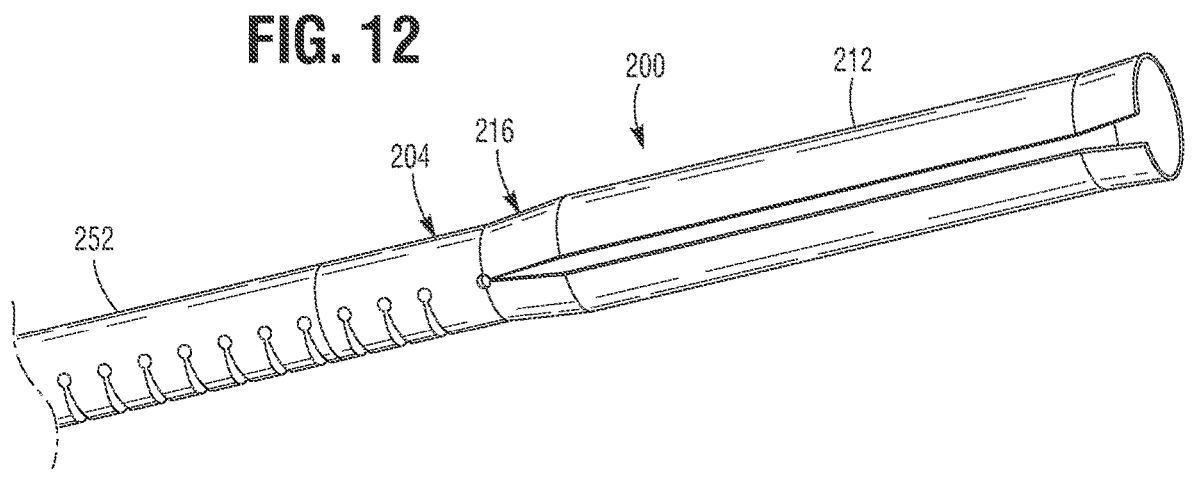
FIG. 12 is a perspective view of another embodiment of a delivery cylinder integrally formed with an outer catheter of a delivery assembly.

The delivery cylinder can be made from a variety of materials, such as any of various biocompatible metal alloys including stainless steel, or nickel titanium ("NiTi") alloys such as Nitinol. In this manner, the strut members 212 can provide axial or columnar strength to the delivery cylinder to resist buckling during loading or recapture of a prosthesis, as further described below. The various features of the delivery cylinder can be fashioned by, for example, laser-cutting the features from a tube. In some embodiments, the delivery cylinder can be integrally formed with a tubular catheter structure such as the outer catheter 252, as shown in FIG. 12, by machining the appropriate features at the distal end of the outer catheter. In this manner, the first tubular portion 204 of the delivery cylinder can be the distal end portion of the outer catheter 252. Alternatively, the delivery cylinder can be separately fabricated and joined to the outer catheter by, for example, welding.

Figure 13:
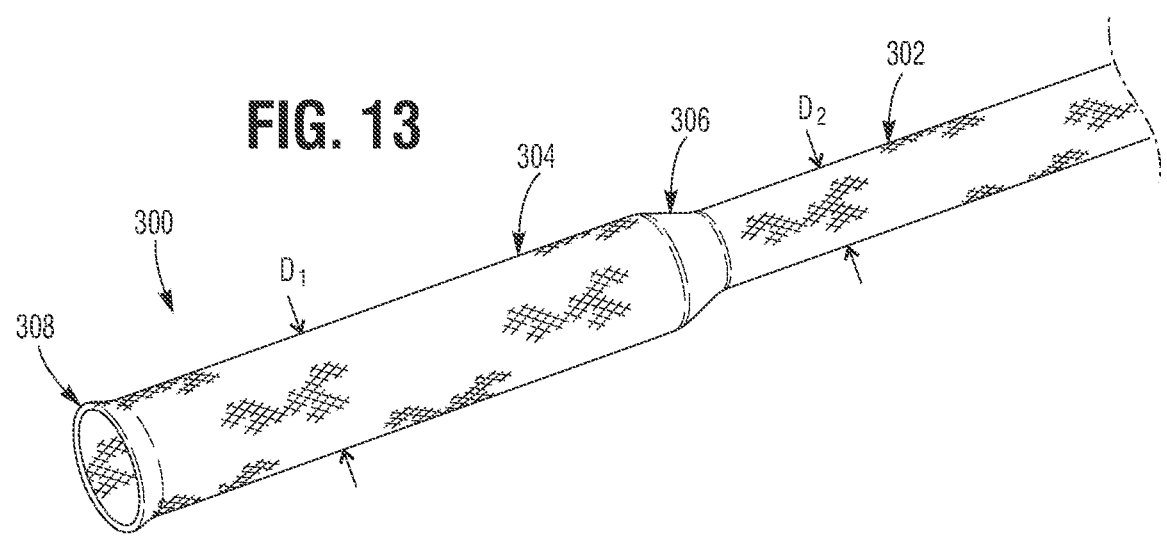
FIG. 13 is a perspective view of a representative embodiment of a woven liner.

In some embodiments, the delivery cylinder 200 can be used in combination with a woven fabric sleeve or liner 300 illustrated in FIG. 13. The liner 300 can comprise a woven tubular structure having a first or proximal body portion 302 and a second or distal body portion 304 with an intermediate portion 306 disposed therebetween. The distal body portion 304 can have a flared end portion 308 to enable the distal body portion to receive and retain a prosthetic implant in a compressed delivery state. In the illustrated embodiment, the distal body portion can have a diameter $D_1$ that is greater than a diameter $D_2$ of the proximal body portion 302. In some embodiments, the proximal body portion 302 can extend proximally from the delivery cylinder to interface with other components of the delivery assembly, as needed. In other embodiments, the woven liner 300 can comprise a single tubular portion having a substantially uniform diameter.

The woven liner 300 can be made from a woven fabric comprising warp and weft yarns woven in a plain, twill, basket, satin, and/or sateen weave. In certain embodiments, different weaves can be used at different portions of the liner to achieve the desired properties. The warp and weft yarns can comprise natural or polymeric fibers, or combinations thereof. For example, the yarns can be composite yarns with cores comprising high tenacity polyethylene terephthalate (PET) and/or nylon, and outer sheathing comprising higher lubricity materials such as polytetrafluoroethylene (PTFE) to reduce friction (e.g., during valve insertion).

The yarns can also be monofilament yarns or multifilament yarns, depending on the particular characteristics desired. For example, in certain embodiments, monofilament yarns can be used in combination with multifilament yarns to reinforce the strength of the woven liner at particular portions of the woven structure. The yarns can also comprise round cross-sections and/or flat cross-sections. In some embodiments, the woven liner can have a pick density of about 500 picks per inch or more, depending upon the radial strength properties desired. In some embodiments, the woven liner 300 can be made substantially seamlessly on, for example, a circular loom or a shuttle-less loom. Thus, the combination of the above features allows the woven liner to achieve high radial strength with fabric thicknesses of about 0.003 inch or less, which can result in a reduced diameter of a delivery assembly into which the woven liner is incorporated. In alternative embodiments, the woven liner can be a non-fabric polymer layer or or film.

Referring again to FIGS. 5 and 6, the woven liner 300 (illustrated schematically) can be disposed inside the delivery cylinder such that the distal body portion 304 of the liner is located within the second tubular portion 206 of the delivery cylinder 200, although it should be understood that the woven liner can also be disposed about the exterior of the delivery cylinder. In some embodiments, the woven liner 300 can be coupled to the delivery cylinder 200 by, for example, suturing the woven liner to the delivery cylinder through the openings 250. In this manner, when the prosthetic implant 234 is loaded into the delivery cylinder 200, the implant can be received in the woven liner 300, and longitudinal motion of the liner relative to the delivery cylinder can be minimized.

This configuration can provide a number of advantages over known delivery systems. For example, in cases where the prosthetic implant 234 is a self-expanding device, such as a self-expanding prosthetic valve, the crimped implant can exert radially outward force $F_1$ against the walls of the woven liner. Because the woven liner 300 provides high radial strength, the woven liner can retain the implant in the crimped delivery state and reduce the radial loading of the strut members 212. This allows the strut members 212 to be made of reduced thickness materials. For example, in a representative embodiment where the delivery cylinder is made from titanium or a titanium alloy, the wall thickness of the strut members can be about 0.005 inch or less, which can reduce the overall diameter of the loaded delivery cylinder.

This configuration can also provide significant advantages during loading of the implant into the delivery cylinder, introduction of the delivery assembly into the body, and deployment of the implant at the treatment site. For example, by allowing the delivery cylinder to radially expand and contract, the degree of crimping required to insert the prosthetic implant into the delivery cylinder can be reduced because the woven liner and the delivery cylinder can radially expand to accommodate the crimped implant. This can also reduce the radial forces exerted on the liner and the strut members when the delivery cylinder is in an unconfined environment.

The radial flexibility of the woven liner 300 and of the flex regions 216 of the strut members 212 can also allow the second tubular portion 206 to expand or contract to conform to the dimensions of a lumen into which the delivery cylinder is inserted. For example, when the delivery cylinder is inserted into a narrow passage, radially inward force applied to the strut members by the surrounding lumen can cause the flex regions to flex such that the strut members move toward the longitudinal axis 218 of the delivery cylinder to assume the contracted configuration of FIG. 5. This can also further collapse the prosthetic implant within the delivery cylinder, allowing the delivery cylinder to be inserted and advanced through, for example, an introducer sheath or narrow vessels in the body. When the delivery cylinder is advanced into an unconfined or a less confined environment, such as upon exiting an introducer sheath or being advanced through a relatively large vessel (e.g., the aorta), the delivery cylinder can return to the expanded configuration, allowing the implant to expand a limited amount and commensurately reducing the radial forces applied to the woven liner and the strut members by the implant. Thus, the ability to move between an expanded configuration and a contracted configuration enabled by the combination of the woven liner and the strut members allows the delivery cylinder to achieve a reduced diameter during the parts of a procedure where such a reduced diameter is advantageous. The delivery cylinder can then return to an expanded configuration when a reduced diameter is unnecessary, which can reduce the radial loading on the woven liner and the strut members. The woven liner 300 can be used in combination with flexible member 242, or one or the other of these may be used alone.

Figure 14:
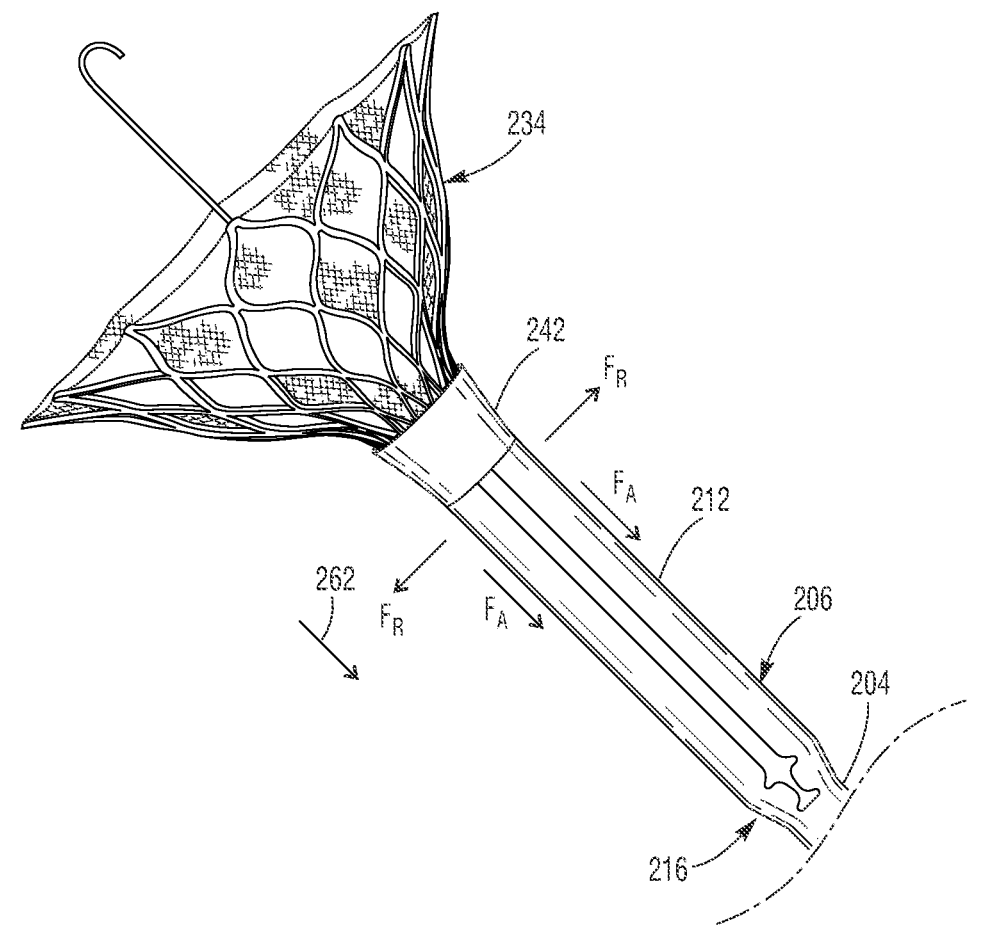
FIG. 14 is a perspective view of a prosthetic implant being recaptured in the delivery cylinder of FIG. 3.
Figures 15, 16:
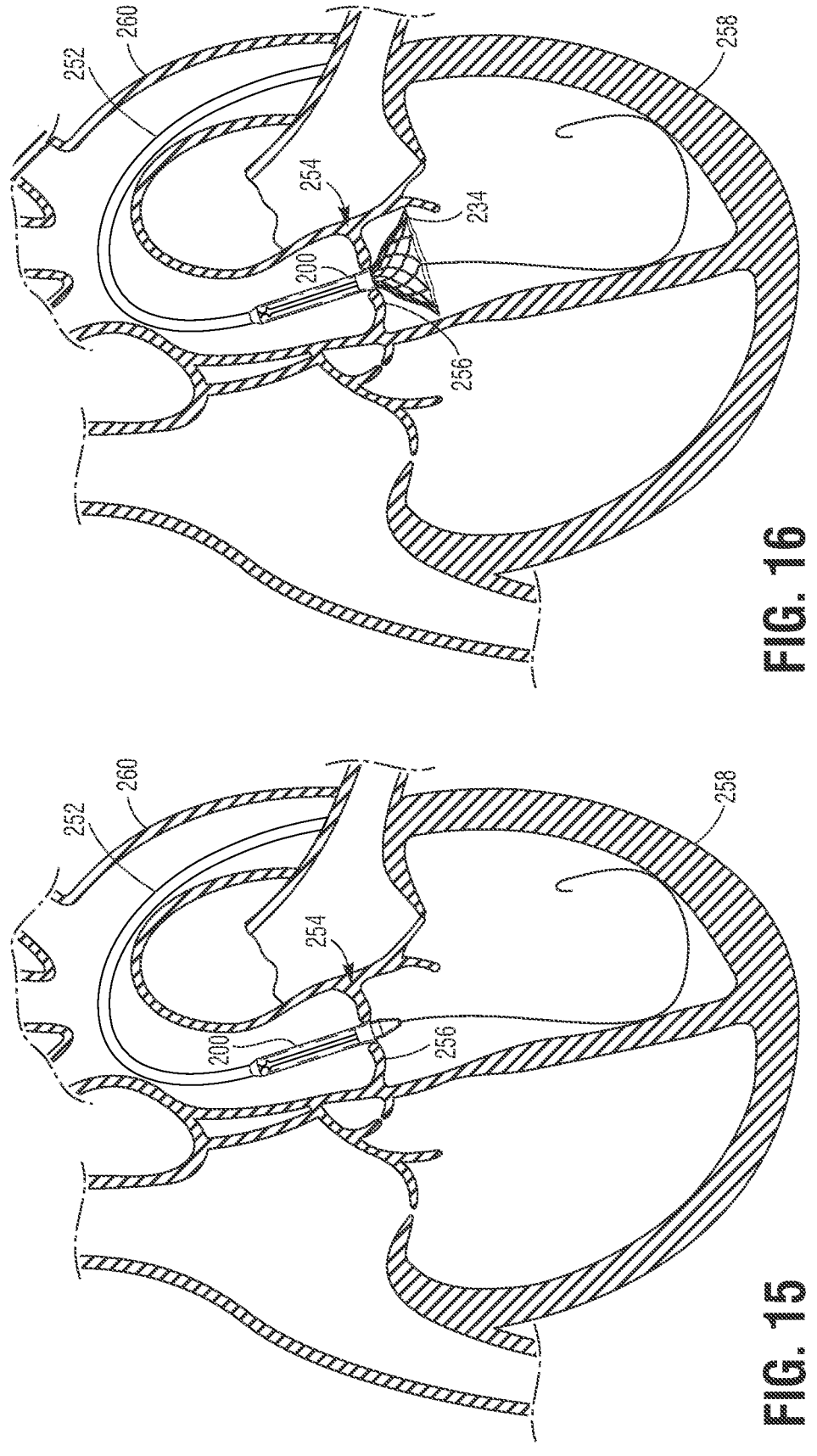
FIGS. 15 and 16 are perspective views illustrating an embodiment of a delivery assembly delivering a prosthetic implant into a patient's heart, shown in partial cross-section.

The combination of the woven sleeve 300 and the strut members 212 of the delivery cylinder 200 can also provide significant advantages during implant/valve deployment and recapture. For example, FIGS. 14, 15, and 16 illustrate implantation of a prosthetic implant 234 configured as a heart valve in a native aortic valve 254 of a heart 258. As illustrated in FIG. 15, the delivery apparatus can be advanced through the aorta 260 until the delivery cylinder 200 is positioned between the leaflets 256 of the aortic valve 254. As the delivery cylinder is advanced through the aorta and positioned in the aortic valve, the delivery cylinder can be in the expanded configuration or in the contracted configuration. The prosthetic valve 234 can then be deployed from the delivery cylinder and can at least partially expand to its functional size, as shown in FIG. 16. As the prosthetic valve 234 deploys, the strut members can transition to the contracted position. Deploying the implant/valve can include advancing the implant from the delivery cylinder or retracting the delivery cylinder proximally with respect to the implant, depending upon the particular system.

During implant/valve implantation, it may become necessary to at least partially recapture the implant/valve (e.g., by partially or fully withdrawing the implant/valve back into the delivery cylinder or advancing the delivery cylinder over the implant/valve) in order to reposition the implant/valve in the delivery position (e.g., in a native heart valve annulus, blood vessel, organ, etc.) or remove the implant/valve from the body. With reference to FIG. 14, when the implant/valve 234 is recaptured, the delivery cylinder can urge the implant/valve back into a collapsed configuration as the implant/valve is drawn back into the cylinder in the direction of arrow 262. During this process, the implant/valve 234 can exert radial forces FR on the woven liner and the strut members 212, causing the flexible member 242 to expand over the implant/valve and causing the strut members to bend at the flex regions 216 such that the delivery cylinder assumes the expanded configuration.

The implant/valve 234 can also exert axial forces FA on the strut members 212. Because a large proportion of the radial forces FR are borne by the woven liner within the second tubular portion 206, and because the woven liner is not axially rigid, the strut members 212 can bear the axial forces FA. Thus, the woven liner and the strut members can act synergistically to facilitate implant/valve recapture because the radial forces can be borne by the woven liner and the axial forces can be borne by the strut members. As stated above, this allows the strut members 212 to be made with a relatively thin wall thickness because the strut members need only provide columnar strength, and need not be configured to bear the full radial forces attendant to compressing the implant back to a collapsed delivery state during recapture.

Figure 17:
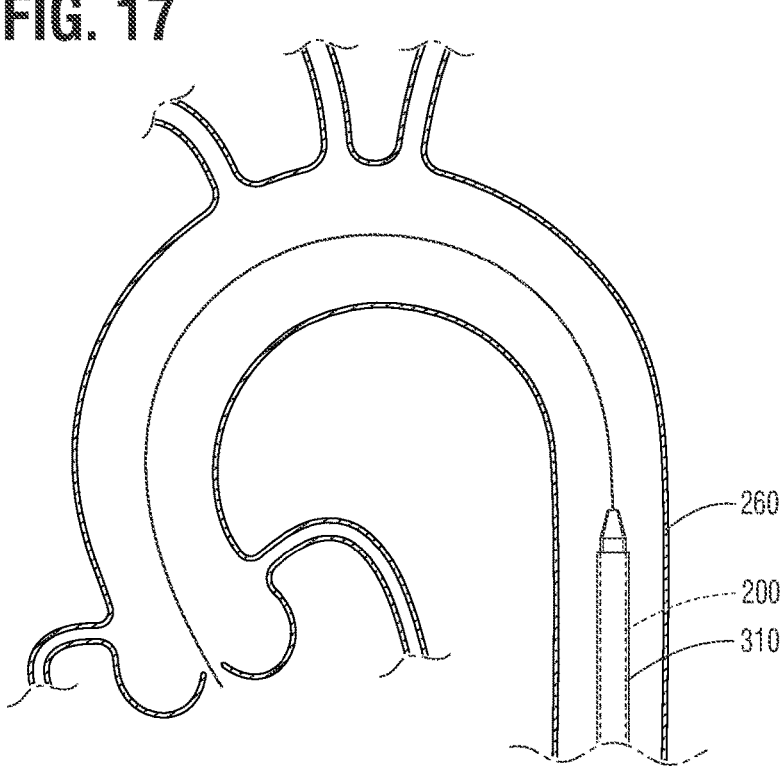
FIG. 17 is a perspective view of another embodiment of a delivery cylinder positioned in a descending aorta with a woven liner disposed over the delivery cylinder.
Figure 18:
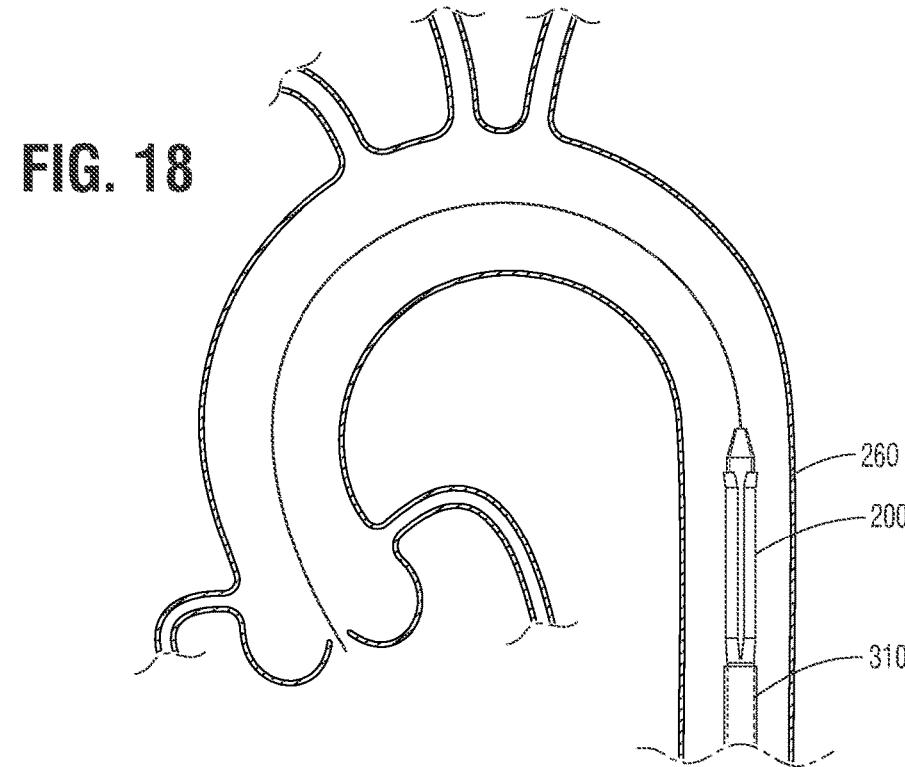
FIG. 18 is a perspective view of the delivery cylinder of FIG. 17 with the woven liner disposed proximally of the delivery cylinder and the delivery cylinder in an expanded configuration.

FIGS. 17 and 18 illustrate an embodiment in which a tubular member, such as a second woven liner 310, is disposed around the exterior of the delivery cylinder 200. In this example, the woven liner 310 can be sized such that the strut members of the delivery cylinder are radially constrained by the woven liner 310 such that the delivery cylinder is in the collapsed configuration for insertion into the body. When the delivery cylinder is advanced to an appropriate location in a relatively wider portion of the patient's vasculature, such as the descending aorta 260, the woven liner 310 can be proximally withdrawn from over the delivery cylinder, as shown in FIG. 18. This can allow the strut members to bend at the flex regions (due to, for example, radial force applied to the strut members and the inner woven liner 300 by the prosthetic implant) such that the delivery cylinder expands to the expanded configuration. Alternatively, instead of withdrawing the woven sheath 310 proximally, the delivery cylinder can be advanced distally out of the woven liner and can move to the expanded configuration. In some embodiments, the tubular member 310 need not be woven, and can be made from any of various materials such as plastics or metals, to constrain the delivery cylinder in the collapsed configuration.

Figure 19:
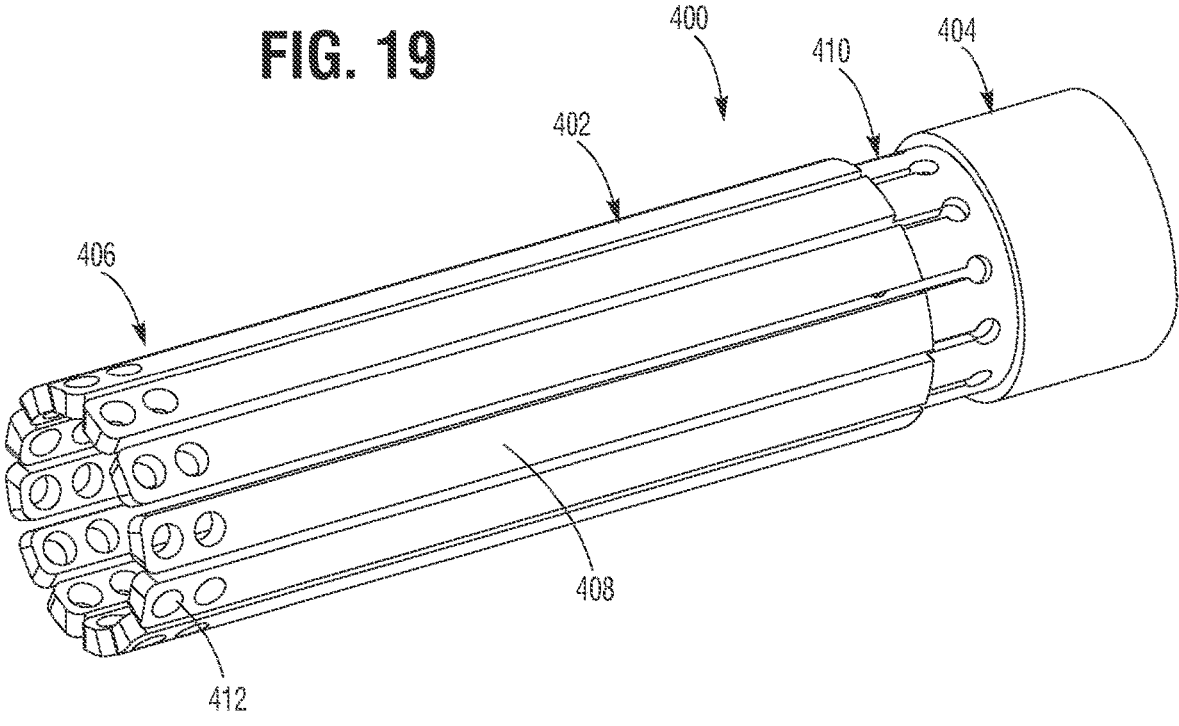
FIG. 19 is a perspective view of another embodiment of a delivery cylinder.

FIG. 19 illustrates another embodiment of a delivery cylinder 400 including a main body portion 402 having a first tubular portion 404 and a second tubular portion 406. The first tubular portion 404 can be couplable to a distal end portion of an outer catheter, similar to the delivery cylinder of FIG. 3 above. The second tubular portion 406 can include a plurality of circumferentially arranged strut members 408 extending from the first tubular portion 404 and having respective flex regions 410 located at the proximal end portions of the strut members. In the illustrated embodiment, the flex regions 410 can have a reduced material thickness as compared to the main body portion of the strut members. This can bias the strut members to bend or flex at the location of the flex regions 410 upon application of radial force, similar to the embodiments described above. In the illustrated embodiment, the delivery cylinder includes 12 strut members 408. However, it should be understood that the delivery cylinder can include any suitable number of strut members. The strut members can also include one or more openings 412 defined at the distal end portions of the strut members to, for example, secure a flexible member on the strut members similar to the flexible member 242. Delivery cylinder 400 can incorporate the same or similar features to those described above with respect to delivery cylinder 200, including a flexible member, one or more liners, openings, extensions, retaining mechanisms, etc.

Figure 20:
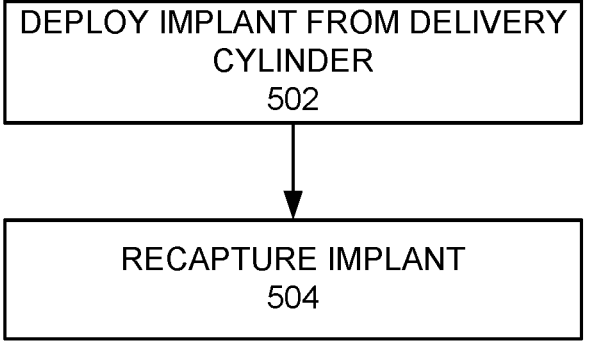
FIG. 20 is a process flow diagram illustrating a representative method of deploying a prosthetic implant.

FIG. 20 illustrates a representative method of recapturing a prosthetic implant with the delivery cylinder embodiments described herein. At a first block 502, a prosthetic implant contained in a delivery cylinder in a radially compressed state can be deployed from the delivery cylinder. The delivery cylinder can include a plurality of circumferentially arranged strut members. As the prosthetic implant is deployed from the delivery cylinder, the implant can at least partially expand to a functional size, and the strut members can move radially inwardly from an expanded configuration to a contracted configuration.

At process block 504, the prosthetic implant can be recaptured such that the prosthetic implant is at least partially returned to the radially compressed state by the delivery cylinder, and the strut members can move radially outwardly such that the delivery cylinder returns to the expanded configuration.

Figure 21:
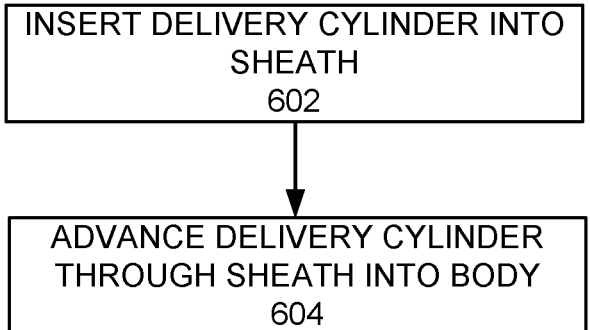
FIG. 21 is a process flow diagram illustrating a representative method of advancing a delivery cylinder through a sheath.

FIG. 21 illustrates a representative method of advancing a delivery apparatus through a sheath, such as an introducer sheath. At process block 602, a delivery assembly including a delivery cylinder containing a prosthetic implant in a radially compressed state can be inserted into an introducer sheath such that a plurality of circumferentially arranged strut members of the delivery cylinder move radially inwardly from an expanded configuration to a contracted configuration to conform to a diameter of the introducer sheath.

At process block 604, the delivery apparatus can be advanced through the introducer sheath and into a patient's body such that the strut members move radially outwardly and return to the expanded configuration.

GENERAL CONSIDERATIONS

It should be understood that the disclosed embodiments can be adapted to delivery and implant prosthetic devices in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed embodiments can also be used to implant prosthesis in other lumens (e.g., blood vessels, etc.) or locations in the body. Further, in addition to prosthetic valves, the delivery assembly embodiments described herein can be adapted to deliver and implant various other prosthetic devices such as stents, grafts, and/or other prosthetic repair devices.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. Features/components described with respect to one exemplary embodiment may be incorporated into other embodiments disclosed herein even if not specifically described with respect to the embodiment.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

As used herein, the terms "integrally formed" and "unitary construction" refer to a construction that does not include any welds, fasteners, or other means for securing separately formed pieces of material to each other.

As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A delivery cylinder for a prosthetic implant, comprising:
    a first tubular portion, wherein a circumference of the first tubular portion is continuous and free of gaps at at least one location along a longitudinal axis of the delivery cylinder in both an expanded configuration and a contracted configuration of the delivery cylinder; and
    a second tubular portion comprising a plurality of distinct strut members coupled to the first tubular portion and defining a volume for containing a prosthetic implant in a radially compressed state, the strut members including proximal end portions and main body portions extending from the proximal end portions in both the expanded configuration and the contracted configuration of the delivery cylinder;
    wherein the delivery cylinder comprises a metal material, and the proximal end portions of each strut member comprise:

a pair of first recessed portions defined in longitudinal edges of the strut member;
    a pair of second recessed portions defined in the longitudinal edges of the strut member distally of the pair of first recessed portions; and
    wherein the pair of first recessed portions reduces a width of the strut member to induce bending of the strut member at a location of the pair of first recessed portions, and the pair of second recessed portions reduces the width of the strut member to induce bending of the strut member at a location of the pair of second recessed portions;
    wherein the strut members are curved in the circumferential direction; and
    wherein the first tubular portion is a distal end portion of an outer shaft of a delivery apparatus.

2. The delivery cylinder of claim 1, wherein the first recessed portions and the second recessed portions are curved.

3. The delivery cylinder of claim 1, wherein the first recessed portions of each strut member are aligned with and open toward first recessed portions of adjacent strut members.

4. The delivery cylinder of claim 3, wherein a distance between opposed first recessed portions of adjacent strut members increases as the delivery cylinder expands from the contracted configuration to the expanded configuration.

5. The delivery cylinder of claim 1, wherein each strut member comprises a pair of extension portions defined in the longitudinal edges of each strut member between the pair of first recessed portions and the pair of second recessed portions.

6. The delivery cylinder of claim 5, wherein a distance between opposed extension portions of adjacent strut members increases as the delivery cylinder expands from the contracted configuration to the expanded configuration.

7. The delivery cylinder of claim 1, wherein opposed first recessed portions of adjacent strut members share a common proximal edge.

8. The delivery cylinder of claim 1, wherein the first recessed portions and the second recessed portions of each strut member are curved in the circumferential direction.

9. A method of using the delivery cylinder of claim 1, comprising:
    retracting a tubular member from over the delivery cylinder of claim 1 or advancing the delivery cylinder through and out of a tubular member such that the plurality of strut members of the delivery cylinder move radially outwardly from the contracted configuration to the expanded configuration; and
    deploying a prosthetic implant contained in the delivery cylinder in a radially compressed state from the delivery cylinder such that the prosthetic implant at least partially expands to a functional size and the strut members move radially inwardly to the contracted configuration while the delivery cylinder remains distal to the tubular member.

10. The delivery cylinder of claim 1, wherein opposed first recessed portions of adjacent strut members share a common proximal edge that is straight in a plan view.

11. The delivery cylinder of claim 1, further comprising a flexible member coupled to distal end portions of the strut members and configured to increase in diameter when the strut members move from the contracted configuration to the expanded configuration.

12. A delivery cylinder for a prosthetic implant, comprising:

a first tubular portion; and a second tubular portion comprising a plurality of distinct strut members coupled to the first tubular portion and defining a volume for containing a prosthetic implant in a radially compressed state, the strut members including proximal end portions and main body portions extending from the proximal end portions in both an expanded configuration and a contracted configuration of the delivery cylinder;

wherein the proximal end portions of each strut member are configured to bend at two locations when the delivery cylinder expands from the contracted configuration to the expanded configuration;

wherein the strut members are curved in the circumferential direction;

wherein in the contracted configuration the first tubular portion and the second tubular portion both comprise a first diameter, and in the expanded configuration the second tubular portion comprises a second diameter along a length of the second tubular portion, the second diameter is greater than the first diameter, and a distal opening in the second tubular portion defined by distal end portions of the strut members comprises the second diameter when the delivery cylinder is in the expanded configuration; and wherein the first tubular portion is a distal end portion of an outer shaft of a delivery apparatus.

13. The delivery cylinder of claim 12, wherein:

each strut member comprises a pair of first recessed portions defined in longitudinal edges of the strut member at a first of the two locations;

each strut member comprises a pair of second recessed portions defined in the longitudinal edges of the strut member distally of the pair of first recessed portions at a second of the two locations; and wherein the pair of first recessed portions reduces a width of the strut member to induce bending of the strut member at the first location of the pair of first recessed portions, and the pair of second recessed portions reduces the width of the strut member to induce bending of the strut member at the second location of the pair of second recessed portions.

14. The delivery cylinder of claim 13, wherein the first recessed portions and the second recessed portions are curved.

15. The delivery cylinder of claim 13, wherein the first recessed portions of each strut member are aligned with and open toward first recessed portions of the adjacent strut members.

16. The delivery cylinder of claim 15, wherein a distance between opposed first recessed portions of adjacent strut members increases as the delivery cylinder expands from the contracted configuration to the expanded configuration.

17. The delivery cylinder of claim 13, wherein each strut member comprises a pair of extension portions defined in the longitudinal edges of each strut member between the pair of first recessed portions and the pair of second recessed portions.

18. The delivery cylinder of claim 17, wherein a distance between opposed extension portions of adjacent strut members increases as the delivery cylinder expands from the contracted configuration to the expanded configuration.

19. The delivery cylinder of claim 13, wherein opposed first recessed portions of adjacent strut members share a common proximal edge.

20. The delivery cylinder of claim 13, wherein the first recessed portions and the second recessed portions of each strut member are curved in the circumferential direction.

* * * * *